(12) United States Patent
Yasuda

(10) Patent No.: US 8,194,252 B2
(45) Date of Patent: Jun. 5, 2012

(54) VARIABLE SPECTROSCOPIC ELEMENT AND ENDOSCOPE SYSTEM HAVING THE SAME

(75) Inventor: Tomoaki Yasuda, Tokyo (JP)

(73) Assignee: Olympus Corporation, Tokyo (JP)

( * ) Notice: Subject to any disclaimer, the term of this patent is extended or adjusted under 35 U.S.C. 154(b) by 423 days.

(21) Appl. No.: 12/445,676

(22) PCT Filed: Oct. 16, 2007

(86) PCT No.: PCT/JP2007/070129
§ 371 (c)(1),
(2), (4) Date: Apr. 15, 2009

(87) PCT Pub. No.: WO2008/047773
PCT Pub. Date: Apr. 24, 2008

(65) Prior Publication Data
US 2010/0296164 A1   Nov. 25, 2010

(30) Foreign Application Priority Data
Oct. 18, 2006   (JP) .................................. 2006-283849

(51) Int. Cl.
*G01B 9/02* (2006.01)
*G01J 3/45* (2006.01)
(52) U.S. Cl. ....................................................... 356/454
(58) Field of Classification Search .......... 359/290–292, 359/321–323, 577–579; 356/450–521
See application file for complete search history.

(56) References Cited

U.S. PATENT DOCUMENTS

| | | | | |
|---|---|---|---|---|
| 4,202,605 A | * | 5/1980 | Heinz | 359/845 |
| 6,819,492 B1 | * | 11/2004 | Picard et al. | 359/579 |
| 2002/0186376 A1 | | 12/2002 | Brown | |
| 2007/0097479 A1 | * | 5/2007 | Yasuda | 359/260 |

FOREIGN PATENT DOCUMENTS

| | | |
|---|---|---|
| JP | 04-098211 | 3/1992 |
| JP | 05-333274 | 12/1993 |
| JP | 09-096768 | 4/1997 |
| JP | 2005-057250 | 3/2005 |
| JP | 2006-023367 | 1/2006 |

* cited by examiner

*Primary Examiner* — Stephone Allen
*Assistant Examiner* — Kimberly N Kakalec
(74) *Attorney, Agent, or Firm* — Scully, Scott, Murphy & Presser, P.C.

(57) ABSTRACT

Light in a desired wavelength band is accurately separated by changing the distance between optical substrates while minimizing deformation thereof. A variable spectroscopic element (1) includes: a plurality of optical substrates (3, 4) opposed to each other with a space therebetween, the optical substrates being provided with coating layers (2a, 2b) on opposed surfaces; actuators (5) arranged circumferentially at intervals around a central axis of the optical substrates (3, 4), the actuators being capable of expansion and contraction in a direction of the gap between the optical substrates (3, 4); and connecting members (10) connecting the actuators (5) and the optical substrates (3, 4) at several locations at intervals in the circumferential direction.

4 Claims, 5 Drawing Sheets

30 : endoscope system
31 : insertion portion
31a : tip
32 : image acquisition unit
33 : light source unit
34 : control unit
35 : display unit
36 : light guide
37 : illumination-light light source
38 : light source control circuit
41 : image acquisition-device driving circuit
42 : variable spectroscopic element control circuit
43 : frame memory
43a : first frame memory
43b : second frame memory
44 : image control circuit

VARIABLE SPECTROSCOPIC ELEMENT AND ENDOSCOPE SYSTEM HAVING THE SAME

TECHNICAL FIELD

The present invention relates to a variable spectroscopic element and an endoscope system having the same.

BACKGROUND ART

Conventionally, a variable spectroscopic element that varies the wavelength of light transmitted therethrough, in which a pair of optical substrates are opposed to each other and the distance between the optical substrates is changed by activating actuators disposed between the optical substrates, is known (for example, refer to Patent Document 1).

The variable spectroscopic element disclosed in Patent Document 1 varies the wavelength band of separated light by activating a plurality of circumferentially spaced actuators to elastically deform an elastically deformable connecting member, moving optical substrates mounted to the connecting member to change the distance between the optical substrates.

PATENT DOCUMENT 1

United States Patent Application, Publication No. 2002/0186376

DISCLOSURE OF INVENTION

However, the variable spectroscopic element disclosed in Patent Document 1 has a disadvantage in that, because the connecting member connecting the plurality of actuators and the optical substrates is bonded to the optical substrates around the entire circumference thereof, when the actuators are activated to elastically deform the connecting member, the deformation generates stress that deforms the optical substrates. This results in a problem in that the optical substrates cannot maintain their flatness, and, if deformed, the spectroscopic characteristics are changed, making it difficult to accurately separate light in a desired wavelength band.

The present invention has been made in view of the above-described circumstances, and an object thereof is to provide a variable spectroscopic element capable of accurately separating light in a desired wavelength band by changing the distance between optical substrates while minimizing deformation thereof, and to provide an endoscope system having the variable spectroscopic element.

To achieve the above-described object, the present invention provides the following solutions.

The present invention provides a variable spectroscopic element including: a pair of optical substrates opposed to each other with a space therebetween, the optical substrates being provided with coating layers on opposed surfaces; actuators that are arranged circumferentially at intervals around a central axis of the optical substrates and capable of expansion and contraction in a direction of the gap between the optical substrates; and connecting members connecting the actuators and the optical substrates at several locations at intervals in the circumferential direction.

In the above-described invention, the connecting members may be made of an elastic material.

In the above-described invention, a ring-shaped flat plate member that connects the actuators and is made of an elastic material may be disposed between the actuators and the connecting members.

In the above-described invention, the flat plate member and the connecting members may be integrally formed.

In the above-described invention, the flat plate member may be bonded to the actuators, and the connecting members may be connected to the flat plate member at locations other than the locations where the actuators are bonded to the flat plate member.

The above-described invention may further include a base to which the actuators are fixed at one end, and a strut member disposed between the base and the flat plate member to fix them.

The present invention also provides an endoscope system comprising the variable spectroscopic element according to any one of the above-described variable spectroscopic elements.

The present invention provides an advantage in that light in a desired wavelength band can be accurately separated by changing the distance between the optical substrates while minimizing deformation thereof.

Figure 1:
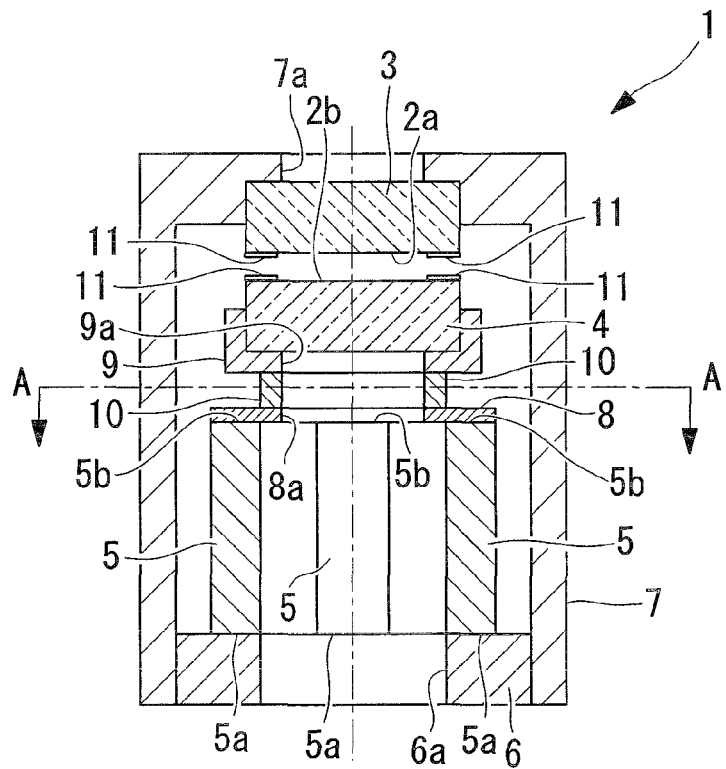
FIG. 1 is a longitudinal sectional view of a variable spectroscopic element according to a first embodiment of the present invention.

EXPLANATION OF REFERENCE SIGNS 1, 20: variable spectroscopic element
2a, 2b: reflective film (coating layer)
3, 4: optical substrate
5: actuator
6: base
8: flat plate member
10: connecting member
21: strut (strut member)
30: endoscope system

BEST MODE FOR CARRYING OUT THE INVENTION

Figure 2:
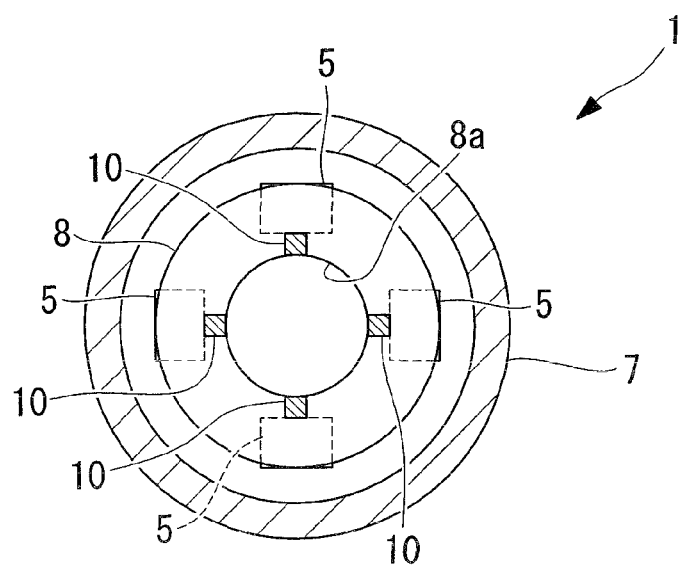
FIG. 2 is a lateral sectional view of the variable spectroscopic element shown in FIG. 1, taken along line A-A.

Referring to FIGS. 1 and 2, a variable spectroscopic element 1 according to an embodiment of the present invention is described below.

As shown in FIG. 1, the variable spectroscopic element 1 according to this embodiment includes two disc-shaped optical substrates 3 and 4 that are opposed substantially in parallel to each other with a slight space therebetween and have reflective films (coating layers) 2a and 2b, respectively, in the area of the optically effective diameter of the opposed surfaces, and four actuators 5 that are arranged circumferentially at intervals outside the area of the optically effective diameter of the optical substrates 3 and 4 and that are made to expand or contract in the direction of the gap between the optical substrates 3 and 4 in response to a voltage signal applied thereto.

The variable spectroscopic element 1 according to this embodiment includes a base 6, to which the four actuators 5 are each fixed at one end (fixed end) 5a, and a casing 7 fixed to the base 6. A ring-plate-shaped flat plate member 8 having a center hole 8a that is larger than the optically effective diameter of the optical substrates 3 and 4 is bonded to the other end (movable end) 5b of each of the four actuators 5. The base 6 also has a center hole 6a that is larger than the optically effective diameter of the optical substrates 3 and 4.

One optical substrate, 3, is fixed to the casing 7, and the other optical substrate, 4, is retained by the retainer 9.

The casing 7 has a through-hole 7a that is larger than the optically effective diameter of the optical substrate 3. The retainer 9 is also a ring-shaped member having a center hole 9a that is larger than the optically effective diameter of the optical substrate 4. The retainer 9 and the flat plate member 8 are connected by rod-like connecting members 10 that are arranged circumferentially at intervals.

The flat plate member 8 projects radially inwardly further than the inside edges of the actuators 5 so as to have the shape of an inwardly projecting collar. The connecting members 10 are fixed to portions of the flat plate member 8 projecting radially inwardly further than the actuators 5.

The flat plate member 8 is made of an elastic material and is less rigid than the retainer 9 and the connecting members 10. Thus, when bending stress due to expansion and contraction of the actuators 5 acts on the flat plate member 8, the flat plate member 8 bends first to absorb the bending stress, allowing the optical substrate 4 to be supported by the retainer 9 and the connecting members 10 without being deformed.

Capacitance sensing electrodes 11 are arranged circumferentially at intervals outside the optically effective diameter of the optical substrates 3 and 4, in an opposed manner.

The reflective films 2a and 2b are made of, for example, a dielectric multilayer film.

The capacitance sensing electrodes 11 are made of, for example, a metal film. By feeding back signals from the capacitance sensing electrodes 11 to control driving signals to the actuators 5, the adjustment accuracy of the transmission characteristics can be improved.

The actuators 5 are, for example, square-bar-like members composed of piezoelectric elements, and extend or contract the length thereof according to the voltage signals applied thereto.

Accordingly, the variable spectroscopic element 1 can vary the wavelength band of light transmitted therethrough by activating the actuators 5 to change the distance between the optical substrates 3 and 4.

Operation of the thus-configured variable spectroscopic element 1 according to this embodiment is described below.

To vary the wavelength band of light to be separated from incident light with the variable spectroscopic element 1 according to this embodiment, voltage signals are applied to the actuators 5 to expand and contract them. Since the actuators 5 are fixed to the base 6 at the fixed ends 5a, the actuators 5 can expand and contract in a direction in which the movable ends 5b move towards or away from the base 6.

Since one optical substrate, 4, is attached to the movable ends 5b of the actuators 5 via the flat plate member 8, the connecting members 10, and the retainer 9, by expanding and contracting the actuators 5, the flat plate member 8 fixed to the movable ends 5b of the actuators 5, the connecting members 10, the retainer 9, and one optical substrate, 4, can be moved in the thickness direction. On the other hand, since the other optical substrate, 3, is attached to the casing 7 fixed to the base 6, by moving one optical substrate, 4, in the thickness direction, the optical substrate 4 is moved with respect to the optical substrate 3 in the direction in which the distance therebetween is changed.

Thus, the wavelength band of light transmittable through the two optical substrates 3 and 4 can be varied to transmit light in a wavelength band determined according to the distance between the optical substrates 3 and 4.

In this case, in the variable spectroscopic element 1 according to this embodiment, when the four actuators 5, arranged circumferentially at intervals, are simultaneously expanded and contracted by the same amount, the flat plate member 8 is translated without being elastically deformed and while maintaining a flat plate shape. In contrast, when the actuators 5 are expanded and contracted by different amounts, the flat plate member 8 is subjected to bending stress.

Since the flat plate member 8 is sufficiently less rigid than the connecting members 10 and the retainer 9, it deforms in response to the bending stress. Thus, the bending stress generated by the movable ends 5b of the actuators 5 becoming uneven is absorbed by the deformation of the flat plate member 8 and thus sufficiently reduced when propagated to the connecting members 10. Further, because the plurality of connecting members 10 are arranged circumferentially at intervals, the retainer 9 retaining the optical substrate 4 can be supported effectively by four-point contact.

As a result, the bending stress acting from the connecting members 10 to the retainer 9 is sufficiently reduced, preventing deformation of the retainer 9. Accordingly, the optical substrate 4 supported by the retainer 9 can be moved without being deformed and while maintaining high flatness.

Thus, in the variable spectroscopic element 1 according to this embodiment, because the flat plate member 8 absorbs the bending stress, the optical substrate 4 can be moved while maintaining high flatness even if the four actuators 5 are individually driven. Accordingly, even if the actuators 5 expand and contract unevenly due to various factors, such as individual differences of the actuators 5, the optical substrate 4 can be moved without being deformed.

Also in the case where the actuators 5 are individually driven to correct relative inclination of the optical substrates 3 and 4 according to the distances detected at several locations in the circumferential direction of the optical substrates 3 and 4 by the capacitance sensing electrodes 11 provided on the optical substrates 3 and 4, the optical substrate 4 can be moved so as to correct the relative inclination, while maintaining high flatness. Thus, high parallelism between the optical substrates 3 and 4 can be achieved.

That is, the variable spectroscopic element 1 according to this embodiment has an advantage in that the distance between the two optical substrates 3 and 4 can be changed while improving the flatness and the parallelism, thereby improving the transmittance and the spectroscopic performance as a spectroscope.

In this embodiment, the ring-plate-shaped flat plate member 8 arranged so as to connect the movable ends 5b of the four actuators 5 is provided. Instead of this, the flat plate member 8 may be eliminated and the rod-like connecting members 10 may be directly fixed to the movable ends 5b of the actuators 5. In such a case, by adopting connecting members 10 that are less rigid than those according to the above-described embodiment to cause the connecting members 10 to elastically deform and absorb the stress when the positions of the movable ends 5b of the actuators 5 are varied, the stress can be prevented from acting on the retainer 9, and the flatness of the optical substrate 4 can be maintained.

Furthermore, in this embodiment, the flat plate member 8 is projected radially inwardly so as to have the shape of an inwardly projecting collar, and the connecting members 10 are provided at the projected portion. Instead of this, the connecting members 10 may be arranged circumferentially with phases shifted relative to the actuators 5.

Although the foregoing description is directed to the case where the numbers of the actuators 5 and the connecting members 10 are four, the present invention is not limited thereto, so long as two or more actuators 5 and connecting members 10 are arranged at intervals.

Figure 3:
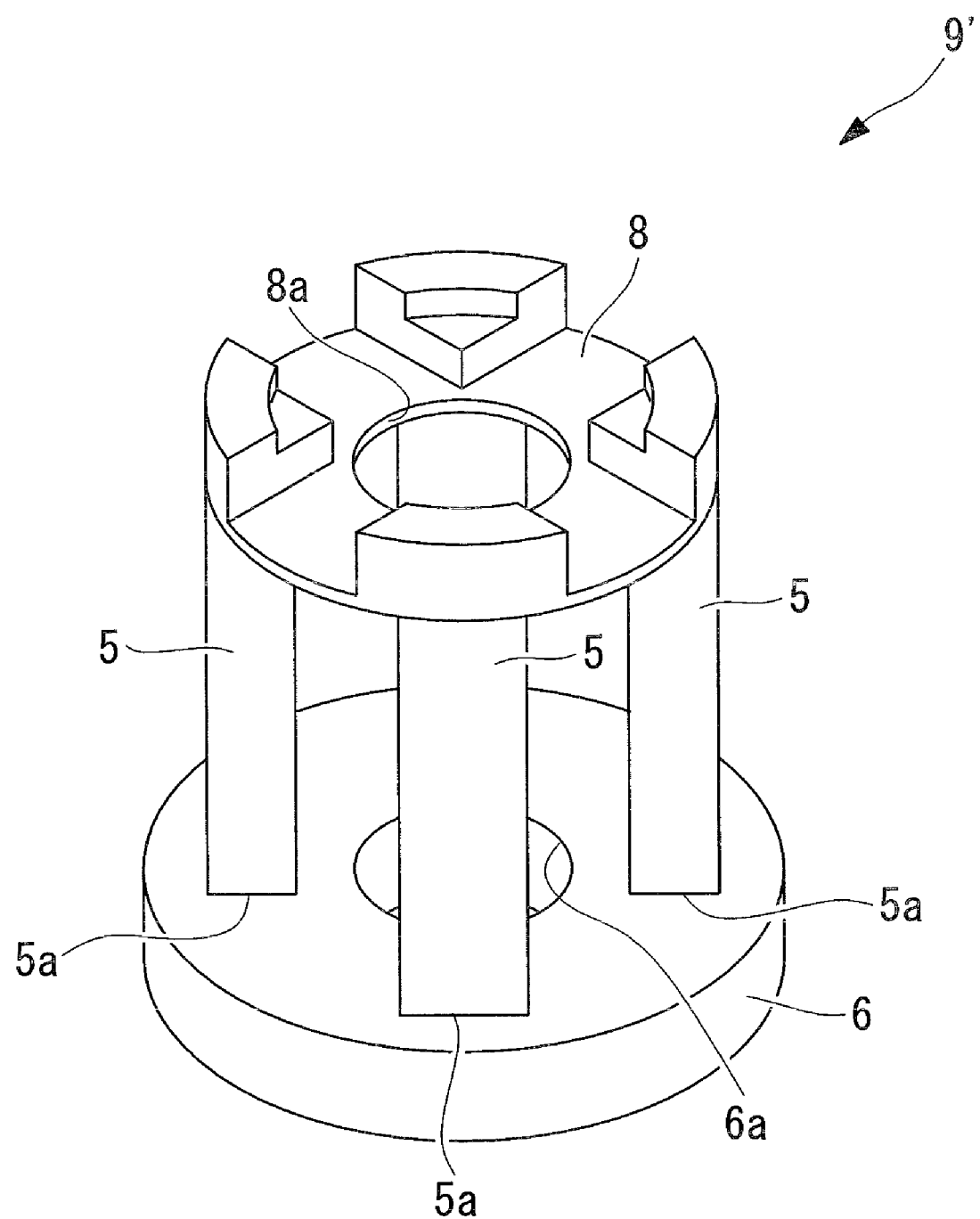
FIG. 3 is a perspective view of a retainer, actuators, and a base used in a modification of the variable spectroscopic element shown in FIG. 1.

This embodiment shows an example in which the ring-shaped retainer 9 and the rod-like connecting members 10 are provided. However, instead of this, as shown in FIG. 3, a retainer 9' may be circumferentially divided and the connecting members 10 may be eliminated. In the example shown in the drawing, the retainer 9' and the flat plate member 8 are integrally formed. Also in this manner, the flat plate member 8 can be elastically deformed to allow the actuators 5 to be individually driven, so as to change the spectroscopic characteristics while maintaining the flatness and parallelism of the optical substrates 3 and 4.

Figure 4:
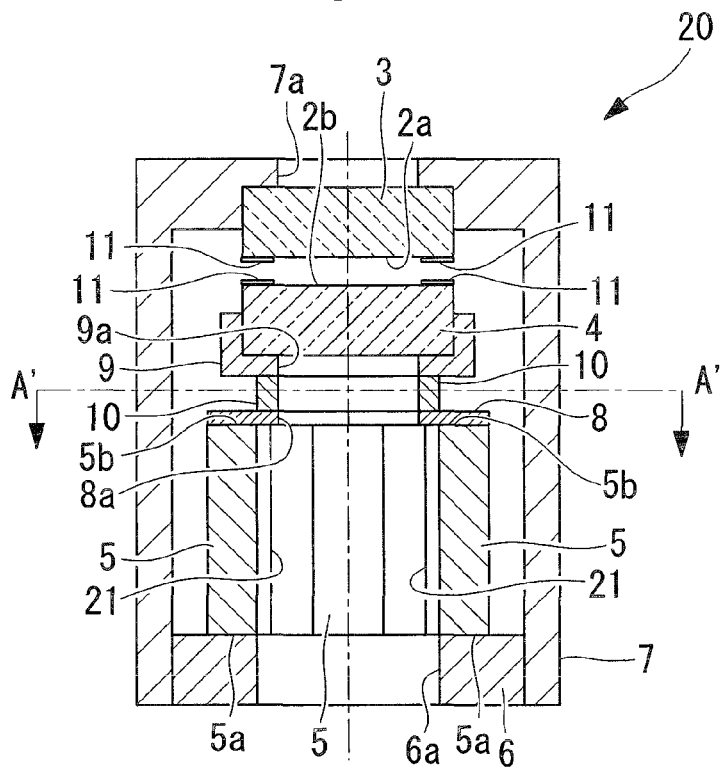
FIG. 4 is a longitudinal sectional view of a variable spectroscopic element according to a second embodiment of the present invention.
Figure 5:
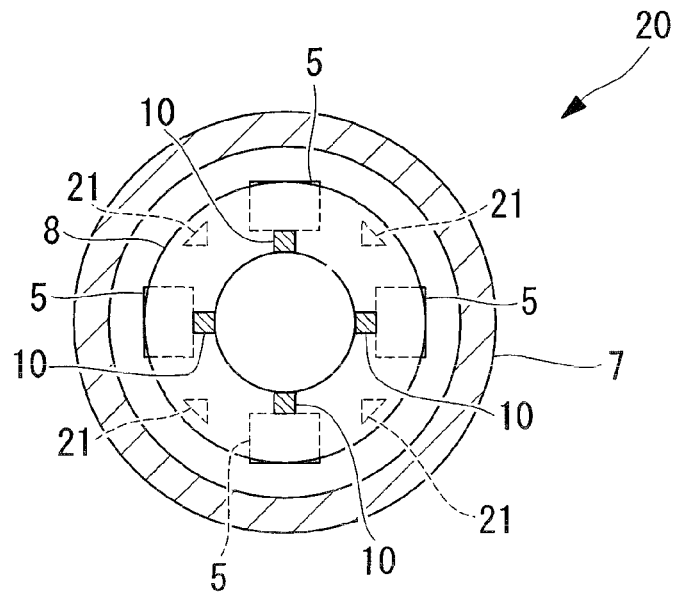
FIG. 5 is a lateral sectional view of the variable spectroscopic element shown in FIG. 4, taken along line A'-A'.

Referring to FIGS. 4 and 5, a variable spectroscopic element 20 according to a second embodiment of the present invention will be described.

In the description of this embodiment, parts having the same configuration as those in the variable spectroscopic element 1 according to the above-described first embodiment are denoted by like reference numerals, and explanations thereof will be omitted.

The variable spectroscopic element 20 according to this embodiment differs from the variable spectroscopic element 1 according to the first embodiment in that struts 21 for connecting the base 6 and the flat plate member 8 are provided therebetween.

In this embodiment, the base 6, the struts 21, and the flat plate member 8 are integrally formed. Although the elastic deformation of the flat plate member 8 is limited to some extent by the struts 21, by configuring the thickness dimension thereof to be sufficiently small, the rigidity is set to a level at which it elastically deforms easily in response to the expansion and contraction of the actuators 5.

The actuators 5 are inserted between the spaces between the base 6, the struts 21, and the flat plate member 8, which are integrally formed, and are bonded to the base 6 at the fixed ends 5a and to the flat plate member 8 at the movable ends 5b.

In the thus-configured variable spectroscopic element 20 according to this embodiment, by integrally forming the flat plate member 8, the base 6, and the struts 21, the flat plate member 8 can be produced while maintaining accurate parallelism with respect to the base 6. Furthermore, inserting the actuators 5 that are slightly shorter than the distance between the flat plate member 8 and the base 6 between the flat plate member 8 and the base 6 and bonding them such that interfaces between the base 6 and the actuators 5 and between the flat plate member 8 and the actuators 5 are filled with an adhesive layer enables assembly while accurately maintaining the parallelism and flatness of the flat plate member 8.

Accordingly, compared with the first embodiment in which the flat plate member 8 is simply bonded to the movable ends 5b of the actuators 5, initial inclination of the flat plate member 8 in the stroke direction of the actuators 5 can be reduced. This minimizes the amount by which the actuators 5 expand or contract so as to eliminate initial inclination of the optical substrate 4 with respect to the optical substrate 3 (in order to eliminate relative initial inclination of the optical substrate 4 with respect to the optical substrate 3) when used as a spectroscopic element. Thus, the strokes of the actuators 5 can be used for the original purpose, that is, varying the distance between surfaces of the optical substrates. As a result, the length of the actuators 5 can be reduced, making the variable spectroscopic element 20 more compact.

Figure 6:
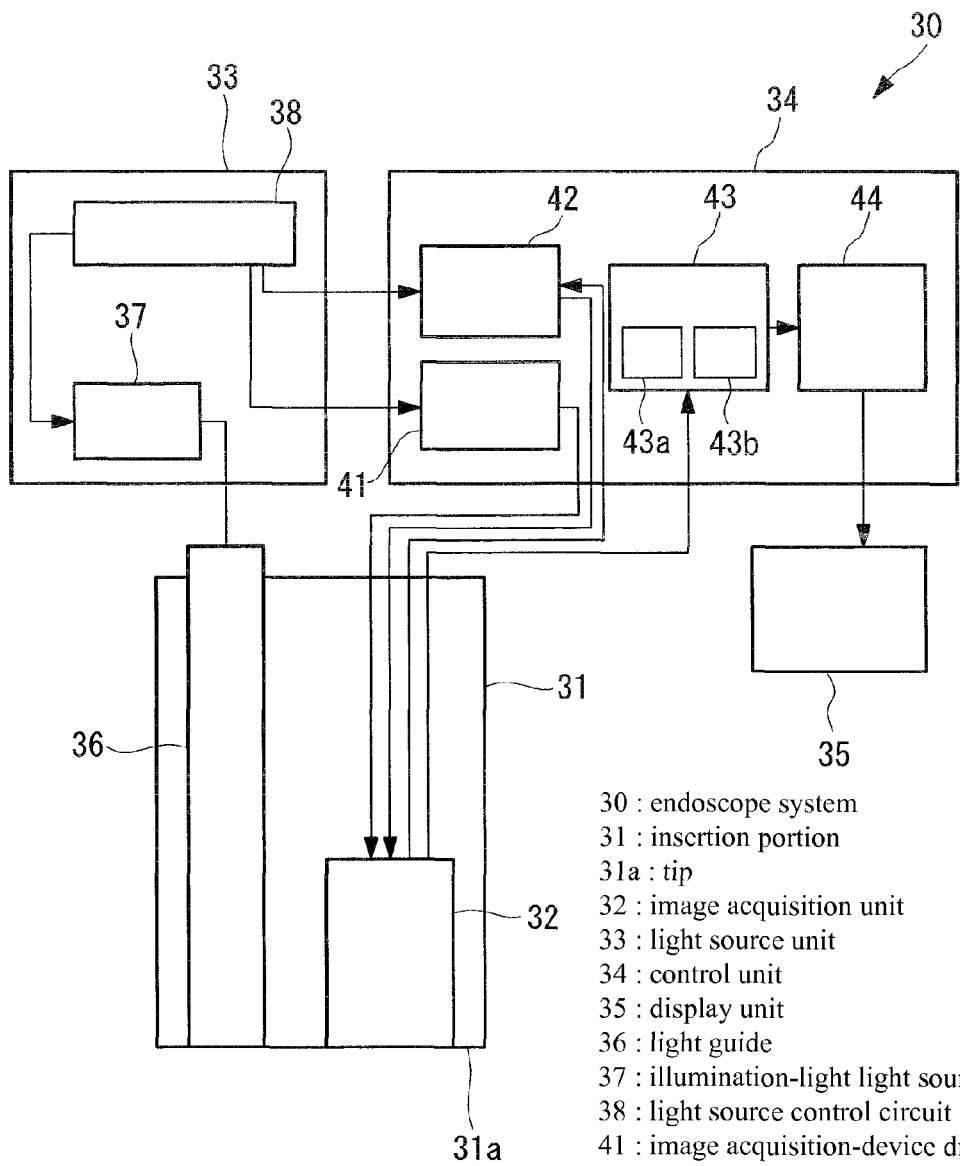
FIG. 6 shows the overall configuration of an endoscope system according to an embodiment of the present invention.

Referring to FIG. 6, an endoscope system 30 according to an embodiment of the present invention is described below.

The endoscope system 30 according to this embodiment includes, as shown in FIG. 6, an insertion portion 31 that is inserted into a body cavity of a living body, an image acquisition unit 32 disposed in the insertion portion 31, a light source unit 33 that generates illumination light, a control unit 34 that controls the image acquisition unit 32 and the light source unit 33, and a display unit 35 that displays an image obtained by the image acquisition unit 32.

The insertion portion 31 has extremely thin outside dimensions such that it can be inserted into the body cavity of the living body, and is provided therein with the image acquisition unit 32 and a light guide 36 that transmits the light from the light source unit 33 to a tip 31a.

The light source unit 33 includes an illumination-light light source 37 that generates illumination light to be emitted on an image-acquisition object in the body cavity so as to excite a fluorescent substance present in the image-acquisition object and generate fluorescence, and a light source control circuit 38 that controls the illumination-light light source 37.

The illumination-light light source 37 is formed by combining a xenon lamp and a bandpass filter (not shown), and the 50% transmission band of the bandpass filter is from 430 to 700 nm. In other words, the illumination-light light source 37 generates illumination light in a wavelength band from 430 to 700 nm.

Figure 7:
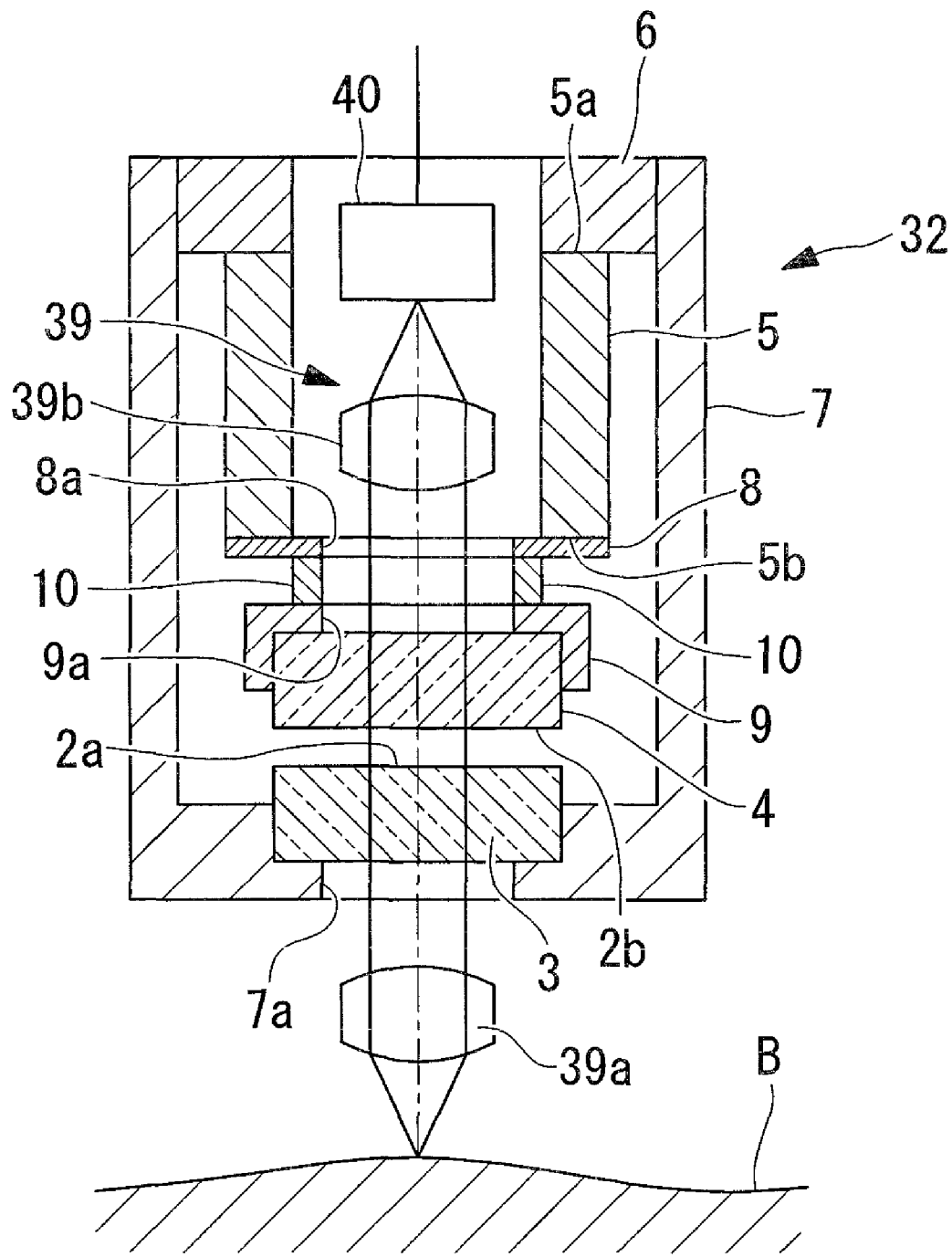
FIG. 7 is a longitudinal sectional view of an image acquisition unit to be installed in the endoscope system shown in FIG. 6.

As shown in FIG. 7, the image acquisition unit 32 includes an image acquisition optical system 39 that focuses light incident from an image-acquisition object B, the variable spectroscopic element 1 according to the first embodiment, whose spectroscopic characteristics can be changed by operating the control unit 34, and an image acquisition device 40 that acquires an image of the light focused by the image acquisition optical system 39 to convert it into an electric signal. Reference numeral 39a denotes a collimating lens, and reference numeral 39b denotes an image forming lens.

The variable wavelength band of the variable spectroscopic element 1 varies between two states according to control signals from the control unit 34.

In a first state, light in a wavelength band from 530 to 560 nm, which corresponds to the range of green visible light, is transmitted (the transmission wavelength band is defined as wavelengths having a transmittance of 50%). In a second state, light in a wavelength band from 630 to 660 nm, which corresponds to the range of red visible light, is transmitted.

As shown in FIG. 6, the control unit 34 includes an image acquisition-device driving circuit 41 that drives and controls the image acquisition device 40, a variable spectroscopic element control circuit 42 that drives and controls the variable spectroscopic element 1, a frame memory 43 for storing image information obtained by the image acquisition device 40, and an image processing circuit 44 for processing the image information stored in the frame memory 43 to output the information to the display unit 35.

The image acquisition-device driving circuit 41 and the variable spectroscopic element control circuit 42 are connected to the light source control circuit 38 and drive and control the image acquisition device 40 and the variable spectroscopic element 1 in synchronization with the activation of the illumination-light light source 37 by the light source control circuit 38.

More specifically, when the variable spectroscopic element control circuit 42 puts the variable spectroscopic element 1 into a first state, the image acquisition-device driving circuit 41 causes the image acquisition device 40 to output the image information to the first frame memory 43a. When the variable spectroscopic element control circuit 42 puts the variable spectroscopic element 1 into a second state, the image acquisition-device driving circuit 41 causes the image acquisition device 40 to output the image information to the second frame memory 43b.

For example, the image control circuit 44 outputs image information received from the first frame memory 43a on a first channel of the display unit 35 and outputs image information received from the second frame memory 43b on a second channel of the display unit 35.

The operation of the thus-configured endoscope system 30 according to this embodiment is described below.

To acquire an image of an image-acquisition object in the body cavity of a living body using the endoscope system 30 according to this embodiment, the insertion portion 31 is inserted into the body cavity, and the tip 31a thereof is placed opposite the image-acquisition object in the body cavity. In this state, the light source unit 33 and the control unit 34 are activated to activate the illumination-light light source 37 in synchronization with the activation of the light source control circuit 38 to generate illumination light.

The illumination light generated in the light source unit 33 propagates through the light guide 36 to the tip 31a of the insertion portion 31 and is emitted from the tip 31a of the insertion portion 31 to the image-acquisition object.

The illumination light is reflected at the surface of the object to be observed, is refracted into a substantially collimated beam by the focusing lens 39a, is transmitted through the variable spectroscopic element 1, and an image is formed by the image forming lens 39b on the image acquisition device 40. Thus, reflected-light image information is obtained.

To obtain reflected-light image information in the green wavelength band, by switching the variable spectroscopic element 1 to the first state using the variable spectroscopic element control circuit 42, the wavelength band of the reflected light reaching the image acquisition device 40 can be limited to 530 to 560 nm. The obtained reflected-light image information is stored in the first frame memory 43a and displayed on the first channel of the display unit 35.

To obtain reflected-light image information in the red wavelength band, by switching the variable spectroscopic element 1 to the second state using the variable spectroscopic element control circuit 42, the wavelength band of the reflected light reaching the image acquisition device 40 can be limited to 630 to 660 nm. The obtained reflected-light image information is stored in the second frame memory 43b and displayed on the second channel of the display unit 35.

Thus, the endoscope system 30 according to this embodiment can provide a user with image information corresponding to different wavelength bands of reflected light.

In this case, the endoscope system 30 according to this embodiment has an advantage in that, because the variable spectroscopic element 1 can be moved while maintaining the flatness and parallelism of the optical substrates 3 and 4, light in a desired wavelength band can be accurately separated from reflected light incident on the image acquisition unit 32 to obtain a sharp spectral image. There is another advantage in that, because the plurality of actuators 5 arranged circumferentially at intervals are individually driven, relative inclination of the two optical substrates 3 and 4 is reduced to achieve high parallelism, making it possible to improve the transmittance and provide a bright spectral image.

If the present invention is not used, methods considered to prevent any influence of the deformation of the optical substrates due to the activation of the actuators include increasing the thickness of the optical substrates to improve the rigidity of the optical substrates and increasing the size of a portion outside the optically effective diameter to reduce distortion at the effective diameter portion. However, these methods increase the size in the optical axis direction or radial direction. The present invention can reduce deformation of the optical substrates without using such methods leading to an increase in size of the optical substrates, which is a big advantage especially for endoscope systems in which reductions in size and diameter are of importance.

In the endoscope system 30 according to this embodiment, the image forming lens 39b and the image acquisition device 40 are disposed radially inward of the actuators 5. However, instead of this, only the focusing lens 39a may be disposed inward of the actuators 5.

Examples of the image acquisition device 40 include a CCD, a CMOS, a photodiode, an electron-multiplier CCD, an electron-bombardment CCD, etc.

Although it has been described that the base 6, the casing 7, and the actuators 5 are bonded with an adhesive, instead of this, for example, they may be fixed with a locking screw or fitted together. Instead of the piezoelectric elements, magnetostrictors may be used as the actuators 5.

The variable spectroscopic element 1 according to this embodiment may be applied not only to the endoscope system 30, but also to a rigid scope or an objective lens for observing the inside of a living body.

The invention claimed is:

1. A variable spectroscopic element comprising:
    a pair of optical substrates opposed to each other with a space therebetween, the optical substrates being provided with coating layers on opposed surfaces;
    a plurality of actuators that are capable of being individually driven and arranged circumferentially at intervals around a central axis of the optical substrates, and capable of expansion and contraction in a direction of the space between the optical substrates;
    connecting members that connect the actuators and one of the optical substrates at several locations at intervals in the circumferential direction;
    a ring-shaped flat plate member that is disposed between the actuators and the connecting members and that is made of an elastic material, and
    a base to which the actuators are fixed at one end,
    wherein the flat plate member is arranged and sandwiched between one of the optical substrates and a side of the actuators opposite to the one end at which the actuators are fixed to the base, and is bonded to the actuators, and the connecting members are connected to the flat plate member at locations other than the locations where the actuators are bonded to the flat plate member.

2. The variable spectroscopic element according to claim 1, wherein the flat plate member and the connecting members are integrally formed.

3. The variable spectroscopic element according to claim 1, further comprising:
    a strut member disposed between the base and the flat plate member to fix them.

4. An endoscope system comprising the variable spectroscopic element according to claim 1.

* * * * *